(12) United States Patent
Drysen

(10) Patent No.: US 7,857,809 B2
(45) Date of Patent: Dec. 28, 2010

(54) INJECTION MOLDED IRRIGATED TIP ELECTRODE AND CATHETER HAVING THE SAME

(75) Inventor: Darrell Drysen, Pasadena, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 645 days.

(21) Appl. No.: 11/322,633

(22) Filed: Dec. 30, 2005

(65) Prior Publication Data
US 2007/0156132 A1 Jul. 5, 2007

(51) Int. Cl.
*A61B 18/18* (2006.01)
(52) U.S. Cl. ............................. 606/41; 606/49; 607/101
(58) Field of Classification Search .................... 606/41, 606/48–50; 607/101–105
See application file for complete search history.

(56) References Cited

U.S. PATENT DOCUMENTS

| | | | |
|---|---|---|---|
| 4,844,099 A * | 7/1989 | Skalsky et al. ............... | 607/120 |
| 5,391,199 A | 2/1995 | Ben-Haim | |
| 5,443,489 A | 8/1995 | Ben-Haim | |
| 5,480,422 A | 1/1996 | Ben-Haim | |
| 5,546,951 A | 8/1996 | Ben-Haim | |
| 5,558,091 A | 9/1996 | Acker et al. | |
| 5,568,809 A | 10/1996 | Ben-haim | |
| 5,643,197 A * | 7/1997 | Brucker et al. ................. | 604/20 |
| 5,797,903 A * | 8/1998 | Swanson et al. ............... | 606/34 |
| 5,843,076 A * | 12/1998 | Webster et al. ................ | 606/41 |
| 5,843,152 A * | 12/1998 | Tu et al. ........................ | 607/122 |
| 5,868,736 A * | 2/1999 | Swanson et al. ............... | 606/34 |
| 5,913,856 A * | 6/1999 | Chia et al. ..................... | 606/41 |
| 6,120,476 A | 9/2000 | Fung et al. | |
| 6,226,554 B1 * | 5/2001 | Tu et al. ........................ | 607/122 |
| 6,371,955 B1 * | 4/2002 | Fuimaono et al. ............. | 606/41 |
| 6,405,078 B1 * | 6/2002 | Moaddeb et al. .............. | 604/21 |
| 6,466,818 B1 * | 10/2002 | Moaddeb et al. .............. | 604/21 |
| 6,475,214 B1 * | 11/2002 | Moaddeb ....................... | 606/41 |
| 6,500,174 B1 * | 12/2002 | Maguire et al. ............... | 606/41 |
| 6,602,242 B1 * | 8/2003 | Fung et al. ..................... | 604/528 |
| 6,611,699 B2 * | 8/2003 | Messing ........................ | 600/372 |

(Continued)

OTHER PUBLICATIONS http://www.cheresources.com/injectionzz.shtml (date as per wayback machine(Jan. 26, 2001), archive.org).*

(Continued)

*Primary Examiner*—Thomas J Sweet
*Assistant Examiner*—Amanda Scott
(74) *Attorney, Agent, or Firm*—Christie, Parker & Hale, LLP

(57) ABSTRACT

A porous tip electrode and a catheter having the same are provided. The catheter generally comprises a catheter body, tip section and control handle. A porous tip electrode, manufactured by injection molding, is mounted at the distal end of the tip section and comprises a main electrode body and a stem. The catheter further comprises a first irrigation tube segment extending through the catheter body and into the proximal end of the tip section, and a second irrigation tube segment extending from the stem of the tip electrode into the distal end of the tip section. Means for energizing saline or other fluid that passes to the tip electrode can include an inner conductive sleeve in the second irrigation tube segment or a conductive material on the stem of the tip electrode. The energized saline ablates lesions in heart tissue.

17 Claims, 15 Drawing Sheets

U.S. PATENT DOCUMENTS

| | | | |
|---|---|---|---|
| 6,671,561 B1* | 12/2003 | Moaddeb | 607/120 |
| 6,852,120 B1* | 2/2005 | Fuimaono | 607/104 |
| 6,986,769 B2* | 1/2006 | Nelson et al. | 606/41 |
| 7,104,989 B2* | 9/2006 | Skarda | 606/41 |
| 7,211,082 B2* | 5/2007 | Hall et al | 606/41 |
| 2002/0183740 A1* | 12/2002 | Edwards et al. | 606/41 |
| 2002/0198520 A1* | 12/2002 | Coen et al. | 606/41 |
| 2003/0004506 A1* | 1/2003 | Messing | 606/41 |
| 2004/0054272 A1* | 3/2004 | Messing | 600/374 |
| 2004/0143258 A1* | 7/2004 | Fuimaono | 606/41 |
| 2004/0267191 A1* | 12/2004 | Gifford et al. | 604/22 |
| 2005/0055019 A1 | 3/2005 | Skarda | |
| 2005/0222564 A1* | 10/2005 | Plaza | 606/41 |
| 2006/0184165 A1* | 8/2006 | Webster et al. | 606/41 |

OTHER PUBLICATIONS http://www.cheresources.com/injectionzz.shtml (date as per wayback machine(Jan. 26, 2001), archive.org) (website is active as of Oct. 21, 2009).*

European Search Report for European Patent Application EP 06 25 6635 completed Apr. 24, 2007.

* cited by examiner

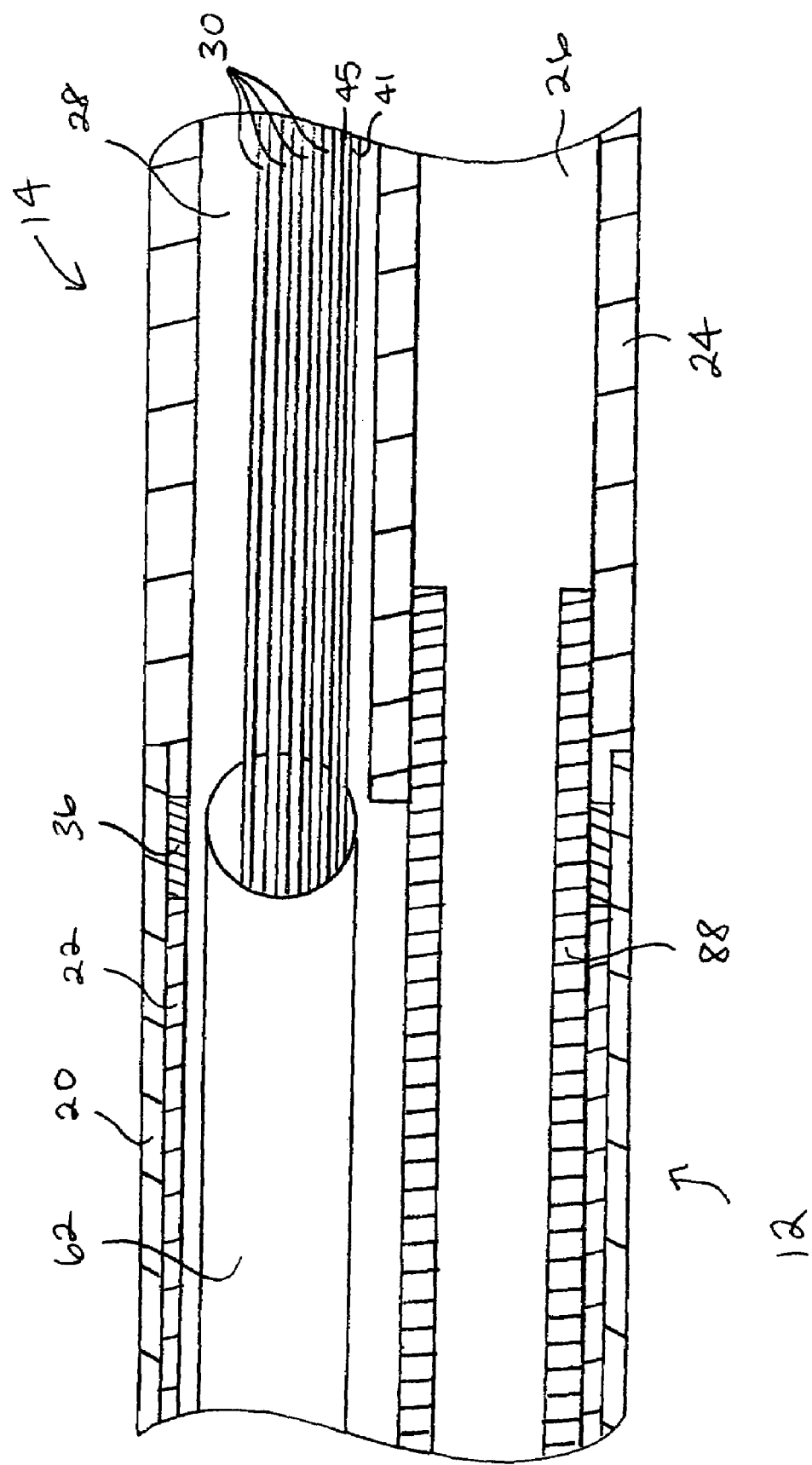

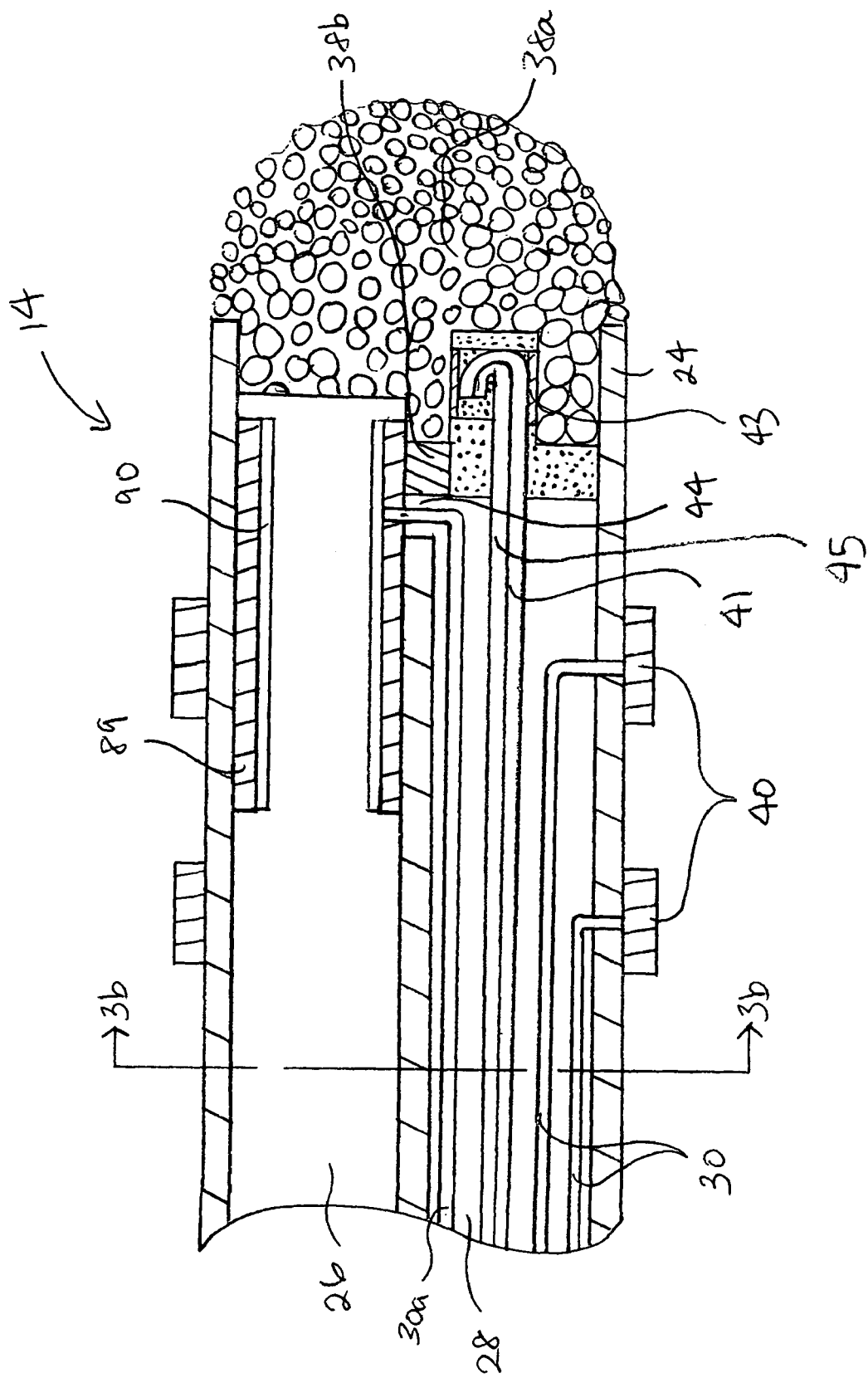

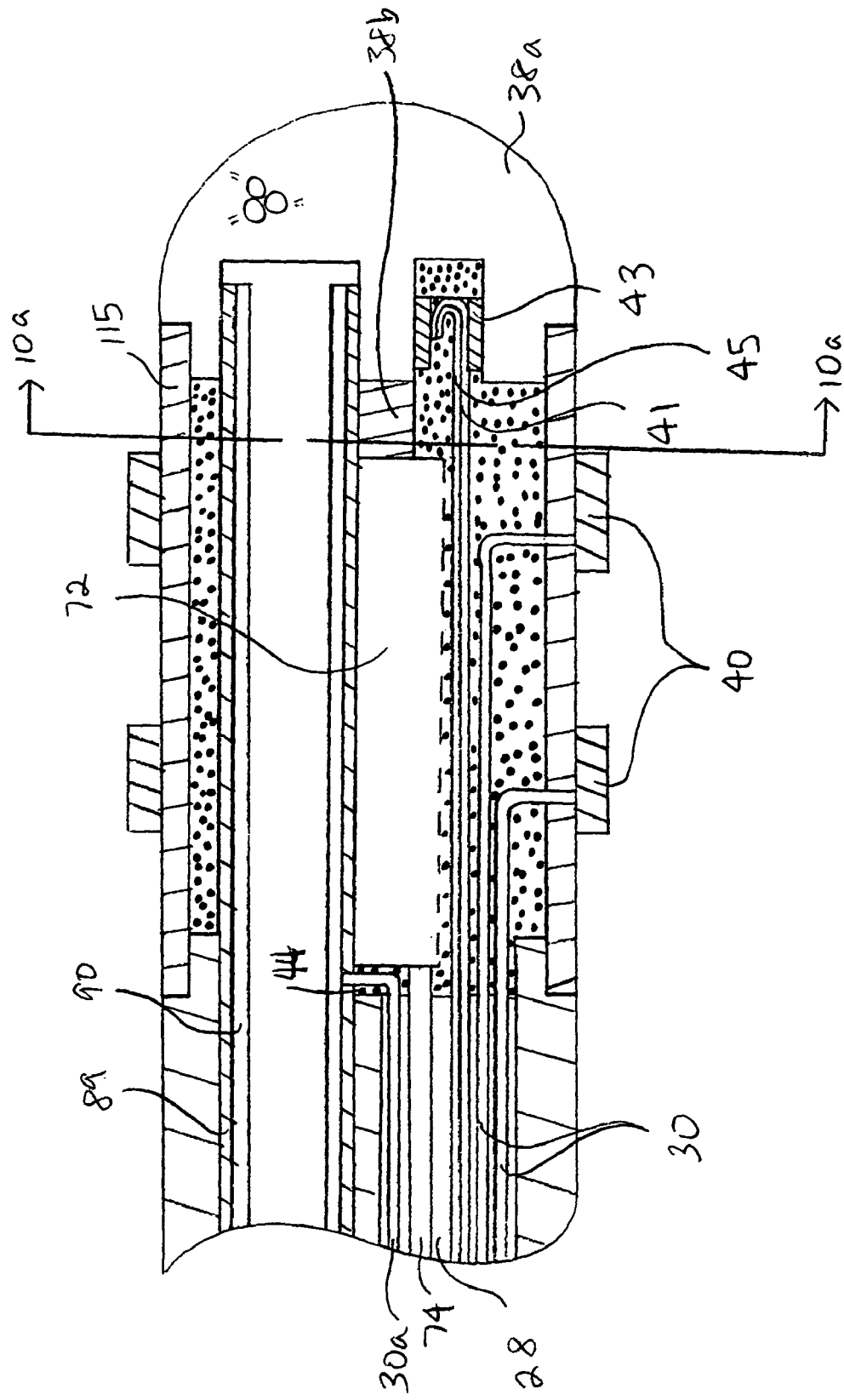

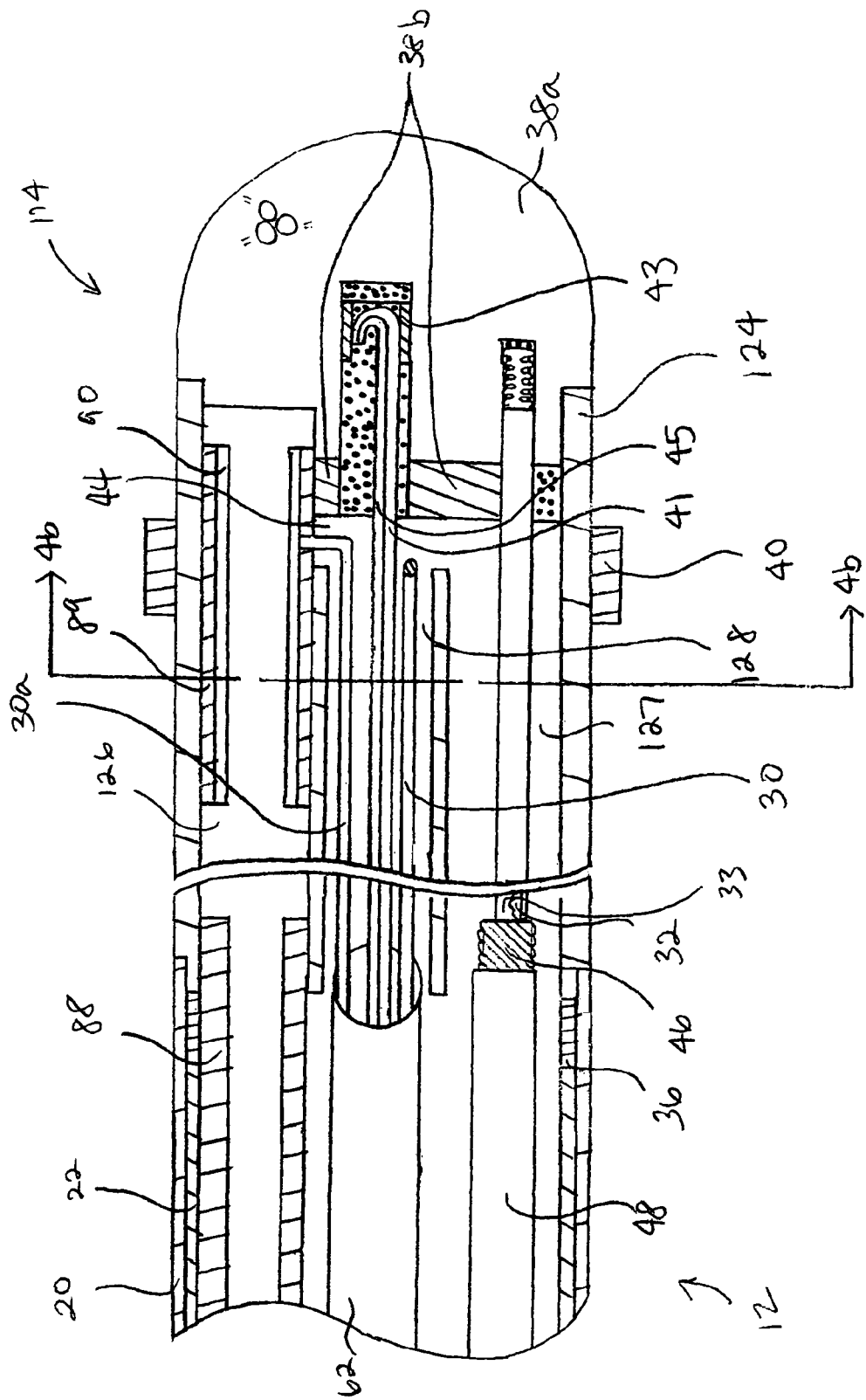

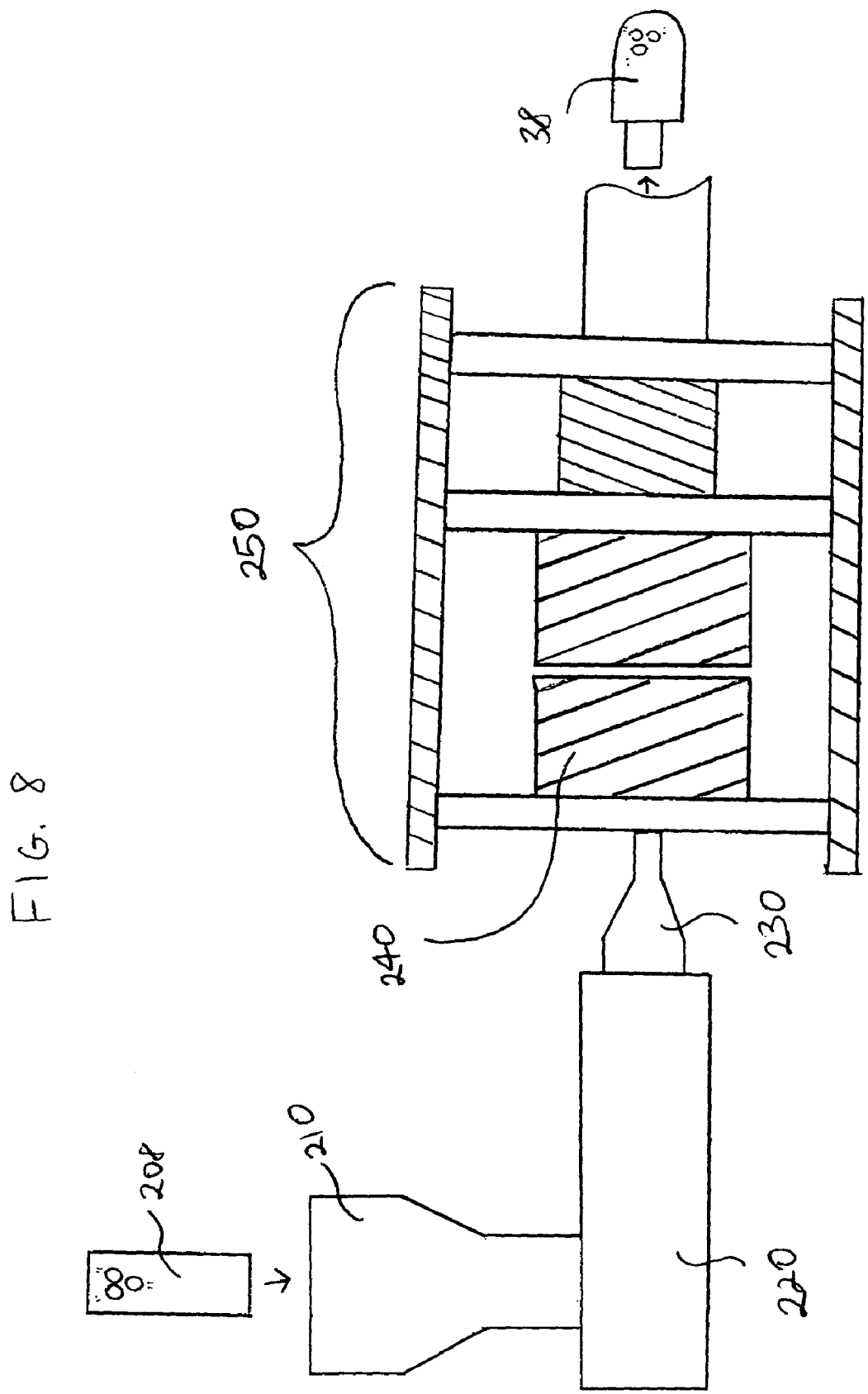

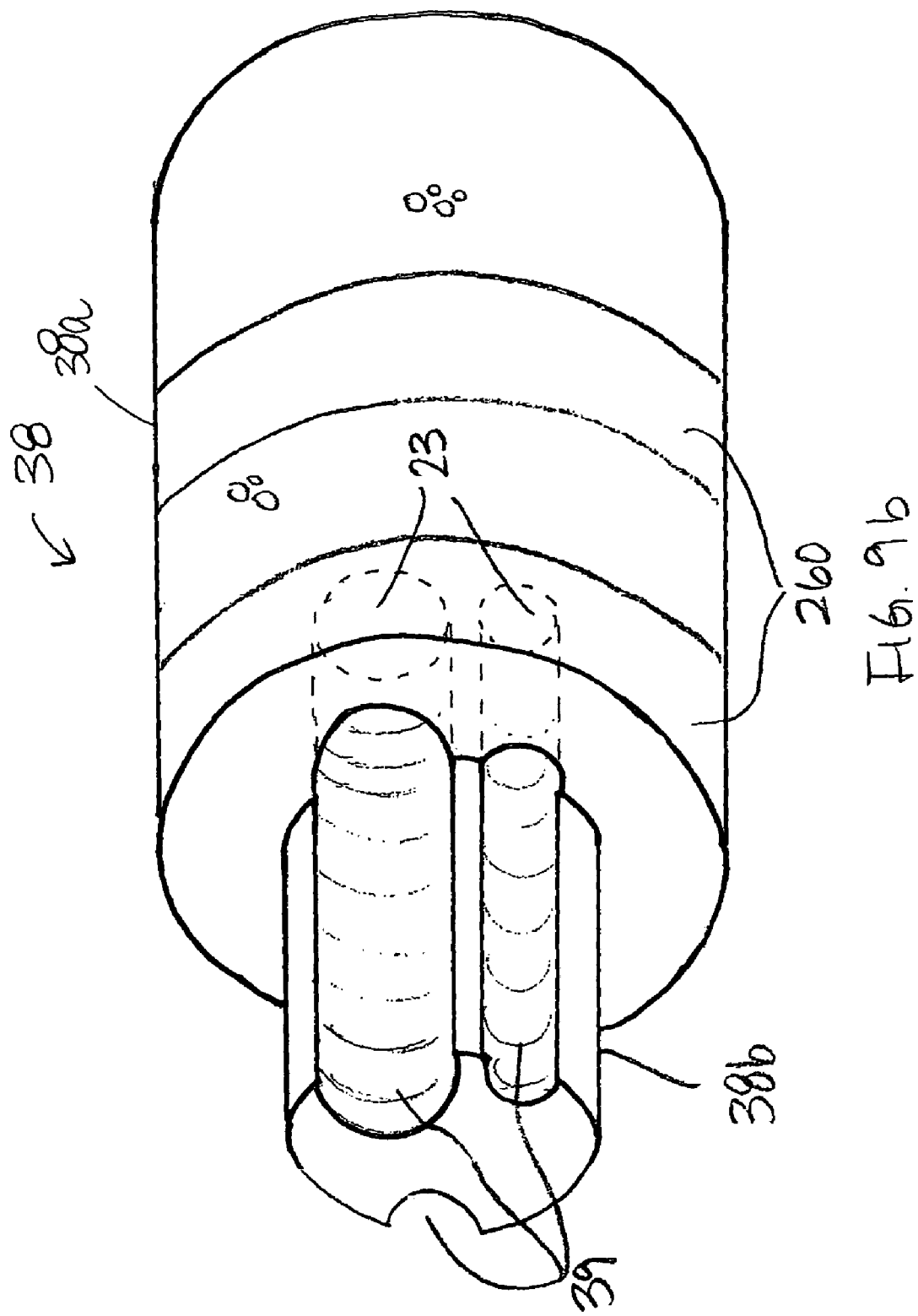

INJECTION MOLDED IRRIGATED TIP ELECTRODE AND CATHETER HAVING THE SAME

FIELD OF THE INVENTION

The invention is directed to injection molded porous tip electrodes and to catheters having the electrodes.

BACKGROUND OF THE INVENTION

Electrode catheters have been in common use in medical practice for many years. They are used to map electrical activity in the heart and to ablate sites of aberrant electrical activity.

In use, the electrode catheter is inserted into a major vein or artery, e.g., the femoral artery, and then guided into the chamber of the heart which is of concern. Within the heart, the ability to control the exact position and orientation of the catheter tip is critical and largely determines the usefulness of the catheter.

In certain applications, it is desirable to have the ability to inject and/or withdraw fluid through the catheter. One such application is a cardiac ablation procedure for creating lesions which interrupt errant electrical pathways in the heart. Traditionally, this has been accomplished with an irrigated tip catheter.

A typical ablation procedure involves the insertion of a catheter having a tip electrode at its distal end into a heart chamber. A reference electrode is provided, generally taped to the patient's skin. Radio frequency (RF) current is applied to the tip electrode, and flows through the surrounding media, i.e. blood and tissue, toward the reference electrode. The distribution of current depends on the amount of electrode surface in contact with the tissue, as compared to blood which has a higher conductivity than the tissue. Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker, resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

In a typical application of RF current to the endocardium, circulating blood provides some cooling of the ablation electrode. However, there is typically a stagnant area between the electrode and tissue which is susceptible to the formation of dehydrated proteins and coagulum. As power and/or ablation time increases, the likelihood of an impedance rise also increases. As a result of this process, there has been a natural upper bound on the amount of energy which can be delivered to cardiac tissue and therefore the size of RF lesions. Historically, RF lesions have been hemispherical in shape with maximum lesion dimensions of approximately 6 mm in diameter and 3 to 5 mm in depth.

In clinical practice, it is desirable to reduce or eliminate impedance rises and, for certain cardiac arrythmias, to create larger lesions. One method for accomplishing this is to monitor the temperature of the ablation electrode and to control the RF current delivered to the ablation electrode based on this temperature. If the temperature rises above a pre-selected value, the current is reduced until the temperature drops below this value. This method has reduced the number of impedance rises during cardiac ablations but has not significantly increased lesion dimensions. The results are not significantly different because this method continues to rely on the cooling effect of the blood which is dependent on the location within the heart and the orientation of the catheter to the endocardial surface.

Another method is to irrigate the ablation electrode, e.g. with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the tip. Effectiveness is achieved by reducing the overall electrode temperature and eliminating hot spots in the ablation electrode which can initiate coagulum formation. More channels and higher flows are more effective in reducing overall temperature and temperature variations, i.e. hot spots. The coolant flow rate must be balanced against the amount of fluid that can be injected into the patient and the increased clinical load required to monitor and possibly refill the injection devices during a procedure. In addition to irrigation flow during ablation, a maintenance flow, typically a lower flow rate, is required throughout the procedure to prevent backflow of blood into the coolant passages. Thus, reducing coolant flow by utilizing it as efficiently as possible is a desirable design objective.

One method for designing an ablation electrode which efficiently utilizes coolant flow is the use of a porous material structure. One such design is described in U.S. Pat. No. 6,405,078 to Moaddeb, et al., the entire content of which is incorporated herein by reference. Moaddeb describes the use of sintered metal particles to create a porous tip electrode. In addition, Moaddeb uses a non-conductive insert implanted into the porous tip electrode for mounted a thermocouple, lead wire and/or irrigation tube within the porous tip electrode. However, during irrigation, the sintered metal particles can disintegrate and break away from the electrode structure. In addition, the metal particles used to create the porous tip electrode are expensive, increasing the manufacturing costs for the catheter. Consequently, a desire arises for a porous electrode having increased structural integrity and decreased production costs.

SUMMARY OF THE INVENTION

While saline has generally been used in irrigated catheters to cool the tip electrode or ablation site, the saline itself can be energized and used to ablate lesions in heart tissue. Accordingly, the present invention is directed to irrigated catheters and porous tip electrodes which use saline as the ablation mechanism.

In one embodiment, the invention is directed to an irrigated catheter having an injection molded porous tip electrode. The catheter comprises a catheter body and a tip section. The catheter body has an outer wall, proximal and distal ends, and a lumen extending therethrough. The tip section comprises a segment of flexible tubing having proximal and distal ends and at least two lumens therethrough. The proximal end of the tip section is fixedly attached to the distal end of the catheter body. The porous tip electrode is fixedly attached to the distal end of the tubing of the tip section. The tip electrode comprises an injection molded porous material through which fluid can pass.

The tip electrode comprises a main electrode body and a stem. At least the main electrode body comprises a porous material. The stem may comprise the same porous material of the main electrode body, or it may comprise a conductive material, such as a metal. Alternatively, the stem may comprise a conductive material coated with the porous material of the main electrode body.

The catheter further comprises first and second irrigation tube segments. The distal end of the first irrigation tube segment is fixedly attached in the proximal end of the tip section, and the proximal end of the first irrigation tube segment terminates in a luer hub in a control handle at the proximal end of the catheter body. The distal end of the second irrigation tube segment is fixedly attached in the tip electrode and the proximal end of the second irrigation tube segment is fixedly attached in the distal end of the tip section.

The second irrigation tube segment may include an inner conductive sleeve connected to a lead wire for energizing the saline or other fluid that passes through the second irrigation tube segment into the porous tip electrode. Alternatively, the conductive sleeve is omitted and the lead wire is connected to the stem of the tip electrode and the saline is energized as it passes through the stem into the main electrode body.

BRIEF DESCRIPTION OF THE DRAWINGS

These and other features and advantages of the present invention will be better understood by reference to the following detailed description when considered in conjunction with the accompanying drawings, wherein:

FIG. 2 is a side cross-sectional view of a catheter body according to one embodiment of the present invention, including the junction between the catheter body and tip section;

FIG. 3a is a side cross-sectional view of the tip section of FIG. 2;

FIG. 3c is a side-cross-sectional view of a tip section according to another embodiment of the present invention;

FIG. 4a is a side cross-sectional view of a tip section according to another embodiment of the present invention, including the junction between the catheter body and tip section;

FIG. 8 is a schematic depicting a device used for injection molding a tip electrode according to one embodiment of the present invention;

FIG. 9b is an elevated side view of a tip electrode according to an alternative embodiment of the present invention;

FIG. 10a is a longitudinal cross-sectional view of the tip section of FIG. 3c taken along line 10a-10a;

DETAILED DESCRIPTION OF THE INVENTION

Figure 1:
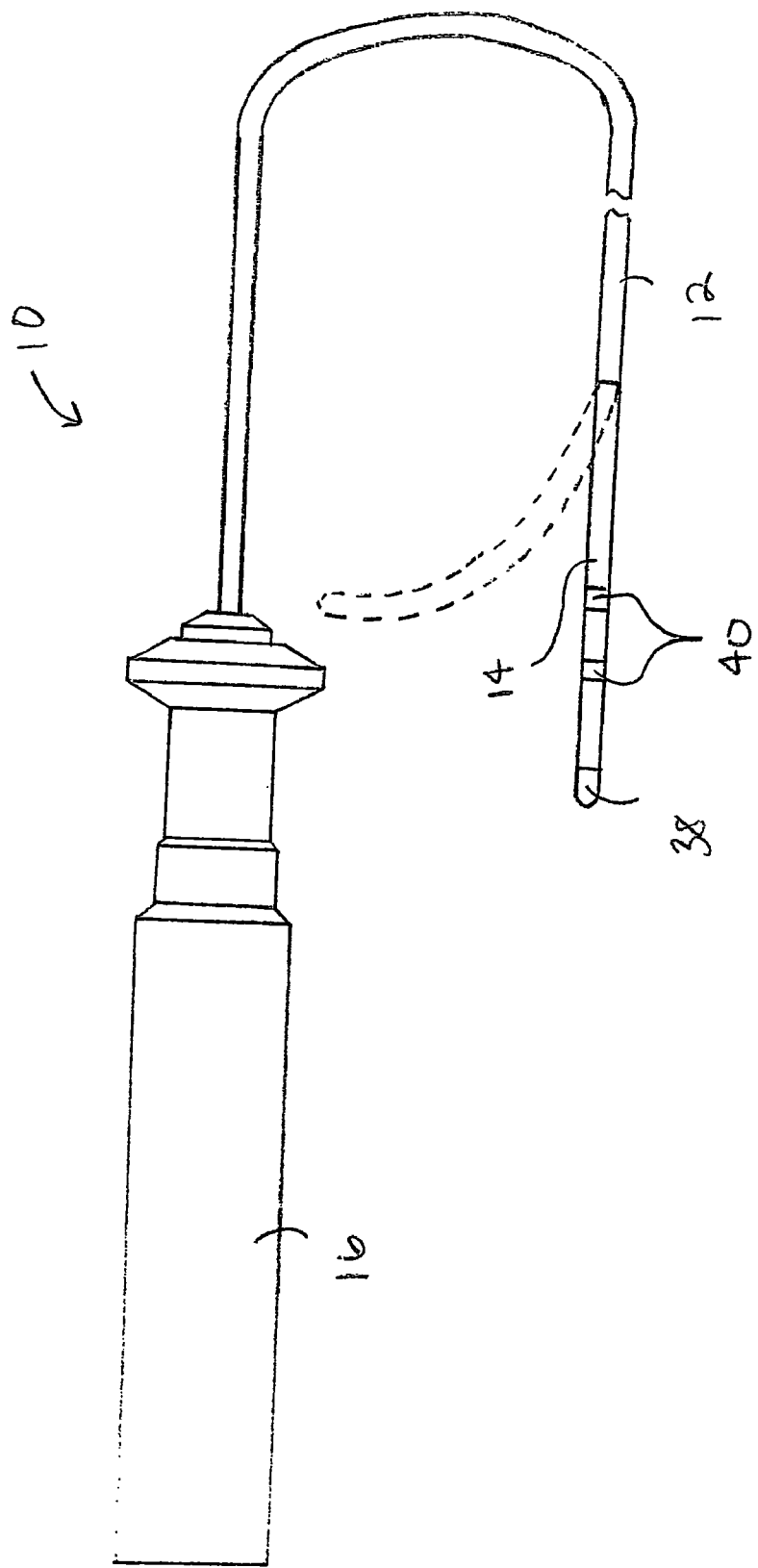
FIG. 1 is an elevated side view of a catheter according to one embodiment of the present invention.

In one embodiment of the present invention, as shown in FIG. 1, a catheter 10 comprises an elongated catheter body 12 having proximal and distal ends, a tip section 14 at the distal end of the catheter body 12, and a control handle 16 at the proximal end of the catheter body 12.

Figure 3B:
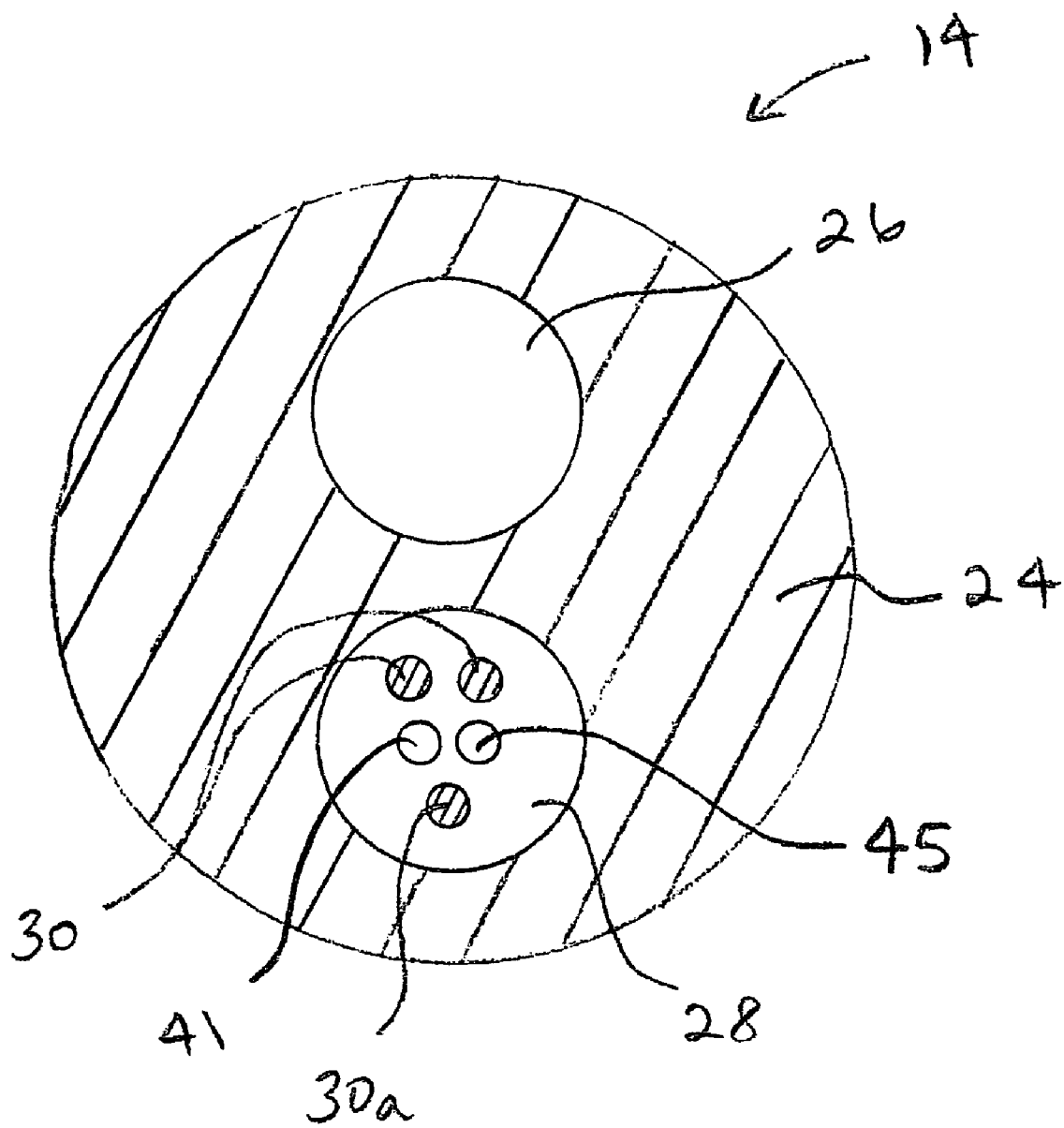
FIG. 3b is a longitudinal cross-sectional view of the tip section of FIG. 3a taken along line 3b-3b.

As shown in FIGS. 2 and 3a, the catheter body 12 comprises an elongated tubular construction having a single axial or central lumen 18. The catheter body is flexible, i.e., bendable, but substantially non-compressible along its length. The catheter body 12 can be of any suitable construction and made of any suitable material. For example, the catheter 10 may comprise an outer wall 20 made of polyurethane or PEBAX. The outer wall 20 can comprise an embedded braided mesh of stainless steel or the like to increase torsional stiffness of the catheter body 12 so that when the control handle 16 is rotated the tip section 14 will rotate in a corresponding manner.

The overall length and diameter of the catheter 10 may vary as desired. In one embodiment, the catheter 10 has an overall length of about 48 inches. The outer diameter of the catheter body 12 is not critical, but in one embodiment is no more than about 8 french. The inner diameter of the outer wall 20 can be lined with a stiffening tube 22, which can be made of any suitable material, such as nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as, or slightly smaller than, the inner diameter of the outer wall 20. In one embodiment, the catheter 10 has an outer diameter of about 0.092 inch and a lumen 18 diameter of about 0.052 inch. If desired, the stiffening tube 22 can be omitted.

The tip section 14 comprises a short section of flexible tubing 24 having at least two lumens. The flexible tubing 24 is made of a suitable non-toxic material that is preferably more flexible than the catheter body 12. One exemplary material for the tubing 24 is braided polyurethane, i.e. polyurethane with an embedded mesh of braided stainless steel or the like. The outer diameter of the tip section 14, like that of the catheter body 12, is no greater than about 8 french. In another embodiment, the tubing 24 is about 6.5 french or less.

In one embodiment, as shown in FIGS. 2, 3a, 3b and 3c, the tubing 24 of the tip section has a first off-axis lumen 26 and a second off-axis lumen 28. The off-axis lumens 26 and 28 extend through diametrically opposed halves of the tip section 14. The first lumen 26 carries an irrigation tube, and the second lumen 28 carries electrode lead wires and temperature sensor wires.

One means for attaching the catheter body 12 to the tip section 14 is illustrated in FIGS. 2 and 3a. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and the catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. A small distance, e.g. about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and while the stiffening tube 22 is under compression, a first glue joint (not shown) is made between the stiffening tube 22 and the outer wall 20 by a fast drying glue, e.g. Super Glue®. Thereafter, a second glue joint is formed between the proximal ends of the stiffening tube 22 and outer wall 20 using a slower drying, but stronger glue, e.g. polyurethane.

A spacer 36 lies within the catheter body 12 between the distal end of the stiffening tube 22 and the proximal end of the tip section 14. The spacer 36 is made of a material that is stiffer than the material of the tip section 14, i.e. polyurethane, but not as stiff as the material of the stiffening tube 22, i.e. polyimide. One suitable material for the spacer 36 is Teflon®. The spacer 36 has outer and inner diameters about the same as the outer and inner diameters of the stiffening tube 22. The spacer 36 provides a transition in flexibility at the junction of the catheter body 12 and the tip section 14 to bend smoothly without folding or kinking. If desired, the spacer can be omitted.

Figure 9A:
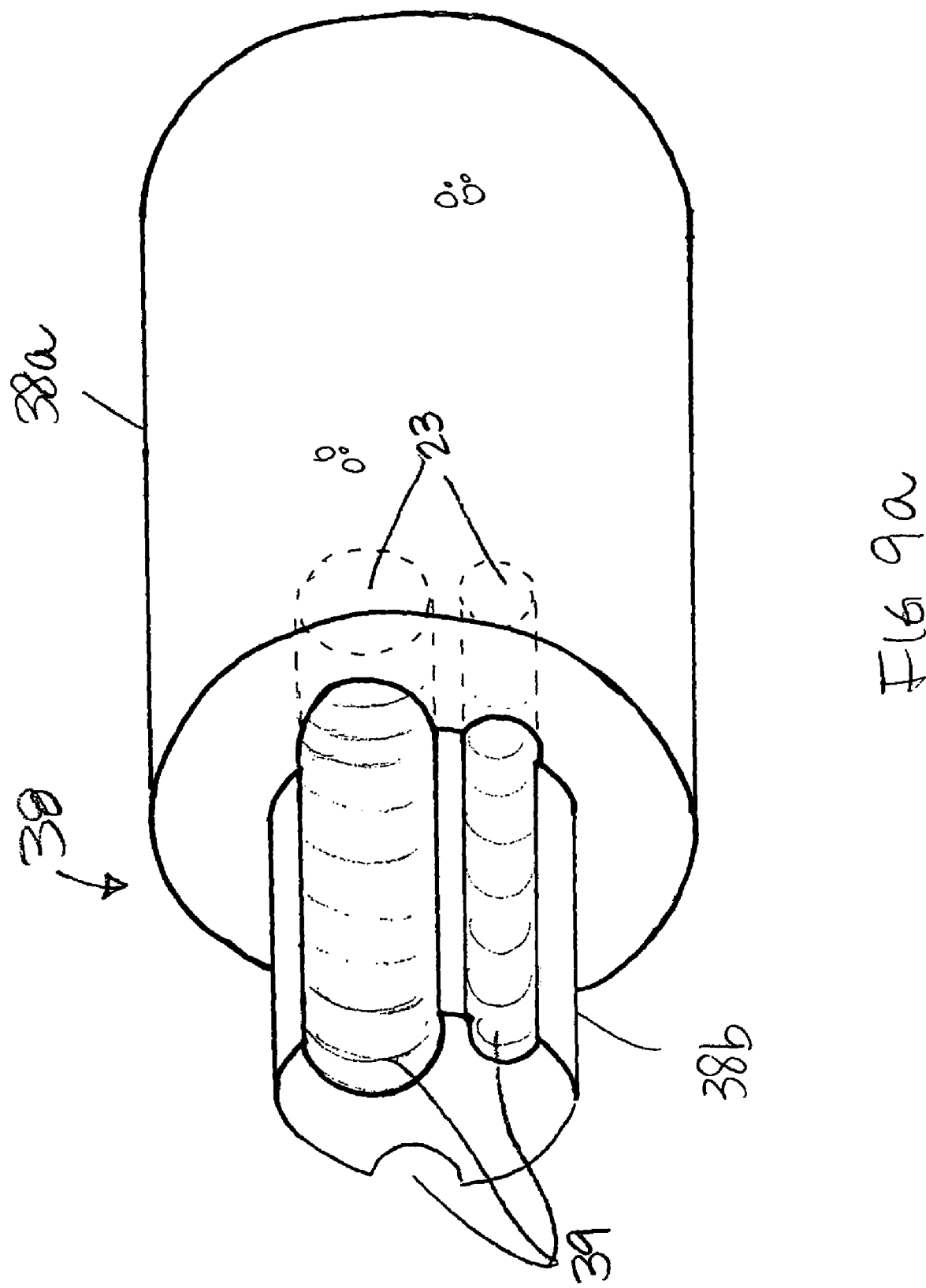
FIG. 9a is an elevated side view of a tip electrode according to one embodiment of the present invention.

The distal end of the tip section carries a tip electrode 38. As shown in FIGS. 9a and 9b, the tip electrode 38 comprises a generally cylindrical main body 38a and a stem 38b. The stem 38b is also generally cylindrical, however, it has indentations 39 in its sides adapted to receive various components of the catheter 10, such as temperature sensor wires, lead wires and an irrigation tube. The indentations 39 in the stem 38b are in communication with blind holes 23 in the main body 38a of the tip electrode 38 into which the components extend.

At least the main body 38a of the tip electrode 38 is made of a porous material. In one embodiment, the main body 38a of the tip electrode 38 comprises a porous material, and the stem 38b comprises a conductive metal, such as platinum. In another embodiment, the main body 38a comprises a porous material and the stem 38b comprises a conductive material overlaid with a porous plastic material. In yet another embodiment, both the main body 38a and the stem 38b comprise the same porous material. Nonlimiting examples of suitable porous materials for the tip electrode 38 include non-toxic porous plastics and polymers, such as polyethylene, polypropylene, ethylene vinyl acetate, polystyrene, epoxy glass, phenol glass and mixtures thereof.

The tip electrode 38 is manufactured by injection molding. Injection molding processes are well-known and any suitable process may be used to form the tip electrodes 38 of the present invention. For example, as shown in FIG. 8, in one embodiment of the injection molding process, the porous material 208 is placed in a hopper 210 which feeds into an injection barrel 220. The injection barrel 220 is heated to soften the porous material. A reciprocating screw (not shown) within the injection barrel pushes the softened porous material through a nozzle 230 at the end of the heated injection barrel 220 which feeds into a closed, cool mold 240. The melted porous material is forced through the nozzle 230 at high pressure into the cool mold 240. The mold 240 is held shut by a clamping unit 250. Once the plastic cools back to a solid state within the mold 240, the mold 240 is opened and the completed tip electrode 38 is removed from the mold 240.

Where the tip electrode 38 has a stem that comprises a conductive metal, it is understood that the injection molding process produces a suitable main electrode body 38a that is fixedly mounted on the stem 38b.

After cooling and removal, the tip electrode 38 has an outer skin 260 which is machined off, increasing the surface porosity of the tip electrode 38. The skin 260 can be completely machined away, maximizing the surface porosity of the tip electrode 38, as shown in FIG. 9a. Alternatively, the skin 260 is only partially machined away, partially increasing the surface porosity of the tip electrode 260, as shown in FIG. 9b. Although FIG. 9b shows a tip electrode 38 having a striped pattern of the skin 260, it is understood that any pattern may be used. The remaining skin 260 on the tip electrode serves to control the flow of saline or other fluid over the tip electrode 38.

As noted above, various components of the catheter 10 (e.g. temperature sensor wires, lead wires and an irrigation tube) extend into the main body 38a of the tip electrode 38 through an indentation 39 in the stem. In the embodiment described above, the tip electrode is manufactured and the stem 38b and the main electrode body 38a are drilled to form the indentations 39 and the blind holes 23. The components are then fixedly attached in the drilled indentations and holes by polyurethane glue or the like when the tip electrode is attached to the tip section 14.

The tip electrode 38 is attached to the distal end of the tip section 14 by inserting the stem 38b into the distal end of the tubing 24 of the tip section 14 and fixing the stem in place with polyurethane glue or the like. As shown in FIGS. 3a, 3c, 4a, 4c, 10a and 10b, there is space between the tubing of the tip section and the stem 38b. As described above, certain components of the catheter 10 may not be completely enclosed in the stem 38a, and the space between the tubing of the tip section and the stem provides room for these components within the tubing of the tip section. The stem is fixed in place in the tubing of the tip section with polyurethane glue or the like.

An irrigation tube is provided within the catheter body 12 for introducing fluids, e.g. saline, to the tip electrode 38. The irrigation tube may be made of any suitable material, such as polyimide tubing. As shown in FIGS. 2, 3a, 3c, 4a and 4c, the irrigation tube comprises a first segment 88 and a second segment 89. The first irrigation tube segment 88 extends through the central lumen of the catheter body 12 and terminates in the proximal end of the first lumen 26 of the tip section 14. The distal end of the first irrigation tube segment 88 is anchored in the first lumen 26 by polyurethane glue or the like. The proximal end of the first irrigation tube segment 88 extends through the control handle 16 and terminates in a luer hub (not shown) or the like at a location proximal to the control handle. The second irrigation tube segment 89 is provided at the distal end of the first lumen 26 and extends into the stem 38b of the tip electrode 38. The second irrigation tube segment 89 is anchored within the first lumen 26 and stem 38b by polyurethane glue or the like.

In use, fluid is injected into the first irrigation tube segment through the luer hub, and flows through the first irrigation tube segment, through the first lumen, through the second irrigation tube segment, into the stem 38b and through the porous material of the tip electrode 38. The fluid is dispersed throughout the interior of the porous material and over all skinless outer surface of the tip electrode 38.

The saline introduced to the tip electrode 38 by the irrigation tube serves as a medium for ablating lesions in heart tissue. To energize the saline for ablation, the second irrigation tube segment 89 is lined on its inner surface with a conductive sleeve 90, as shown in FIGS. 3a and 4a. The sleeve 90 is connected to a lead wire 30a which extends from the second irrigation tube segment 89 to the second lumen 28 of the tip section, through the second lumen 28 and the central lumen 18 in the catheter body 12 and into the control handle 16. The proximal end of the lead wire 30a extends out the proximal end of the control handle 16 and is connected to an appropriate connector (not shown), which can be plugged into or otherwise connected to a suitable monitor, source of energy, etc.

The lead wire 30a is connected to the sleeve 90 by any conventional technique. For example, connection of the lead wire 30a that extends distally from the distal end of the lumen 28 of the tubing 24 of the tip section to the sleeve is accomplished by first making a small hole through the second irrigation tube segment 89 with a needle and heating the needle sufficiently to form a permanent hole. The distal end of the lead wire 30a is then drawn through the hole with a microhook or the like. The distal end of the lead wire 30a is then stripped of any coating and welded to the sleeve 90, which is then slid into place within the second irrigation tube segment 89 and fixed in place with polyurethane glue or the like. The hole in the second irrigation tube segment 89 is plugged with polyurethane glue or the like to prevent leakage of fluid. The proximal end of the lead wire 30a extends from the hole in the second irrigation tube segment 89, through a channel 44 formed between the tip section and stem 38b into the second lumen 28, through the second lumen 28 of the tip section and the central lumen 18 of the catheter body 12, terminating in the control handle 16. In this embodiment, the saline is energized as it passes through the second irrigation tube segment 89.

Figure 4B:
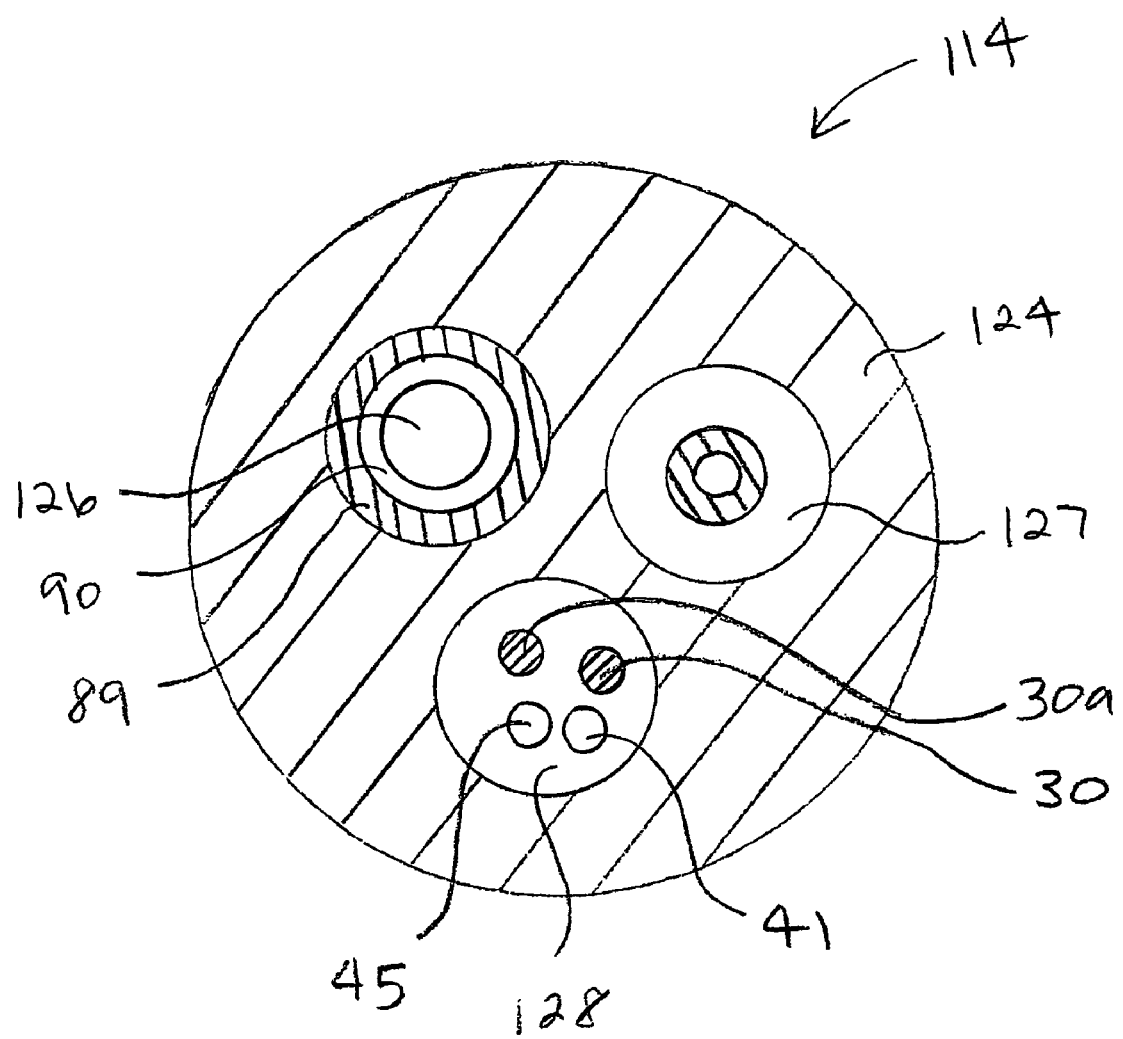
FIG. 4b is a longitudinal cross-sectional view of the tip section of FIG. 4a taken along line 4b-4b.
Figure 4C:
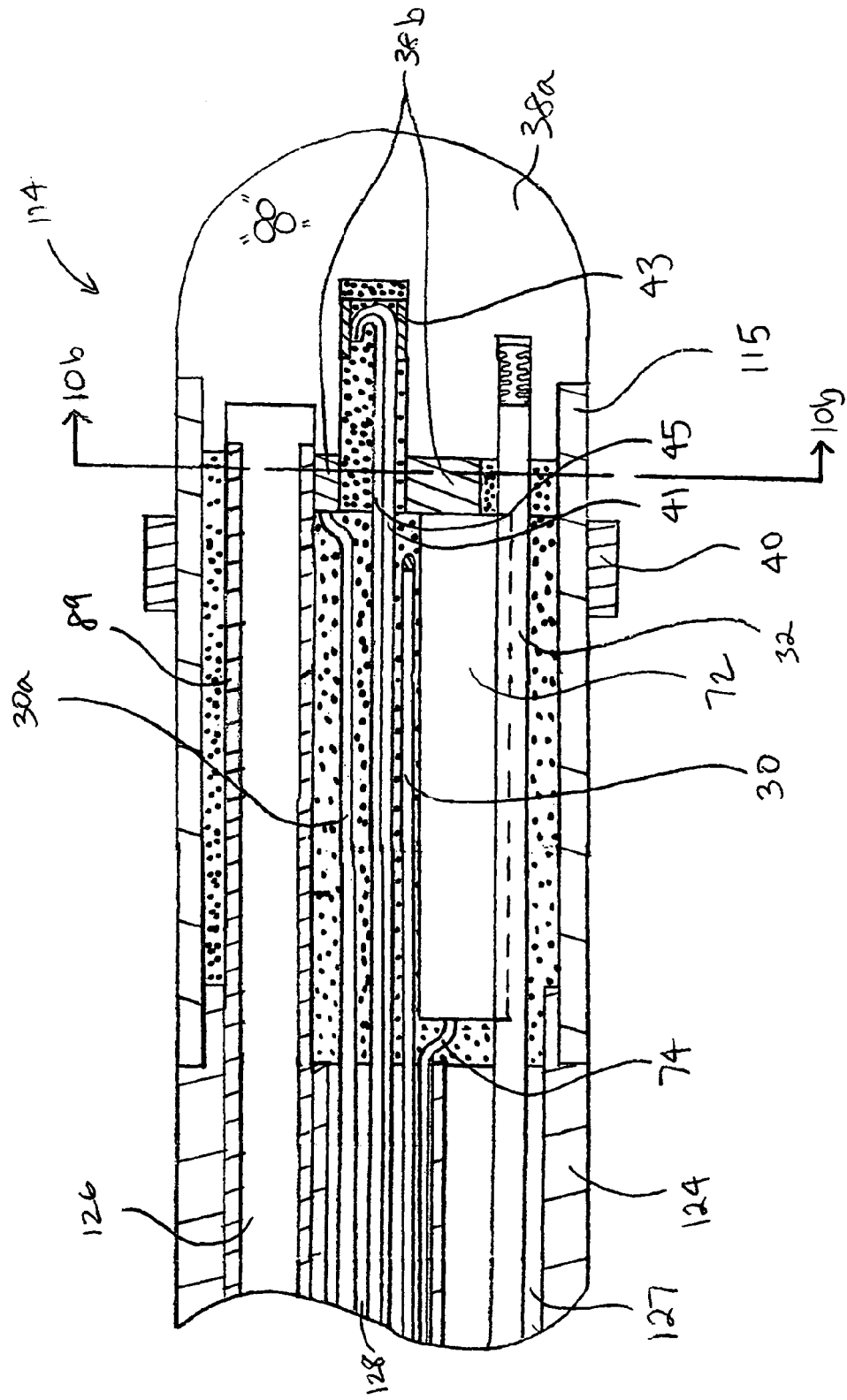
FIG. 4c is a side cross-sectional view of a tip section according to another embodiment of the present invention.

In another alternative embodiment, as shown in FIG. 4c, the sleeve 90 of the second irrigation tube segment 89 is omitted. Rather, the stem 38b of the tip electrode comprises a conductive material, such as platinum or the like. In this embodiment, the lead wire 30a is connected to the conductive material of the stem 38b by welding or the like within a blind hole (not shown) in the stem. The lead wire 30a extends through the second lumen 28 of the tip section 14, through the central lumen 18 in the catheter body 12 and into the control handle. In this embodiment, the saline is energized as it disperses in the porous material of the main body 38a of the tip electrode 38 and comes in contact with the stem 38b of the tip electrode 38.

Figure 10A:
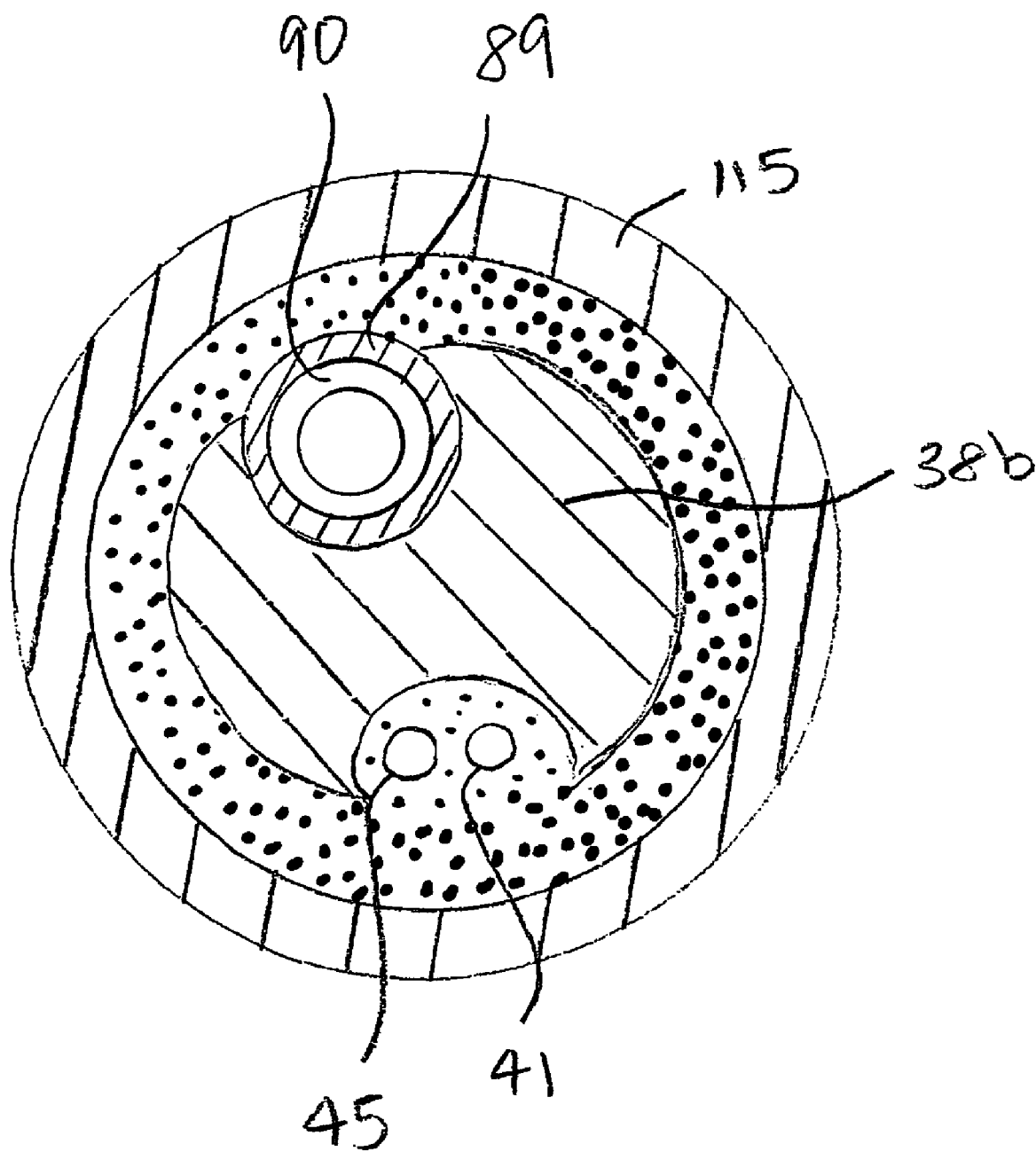
Figure 10B:
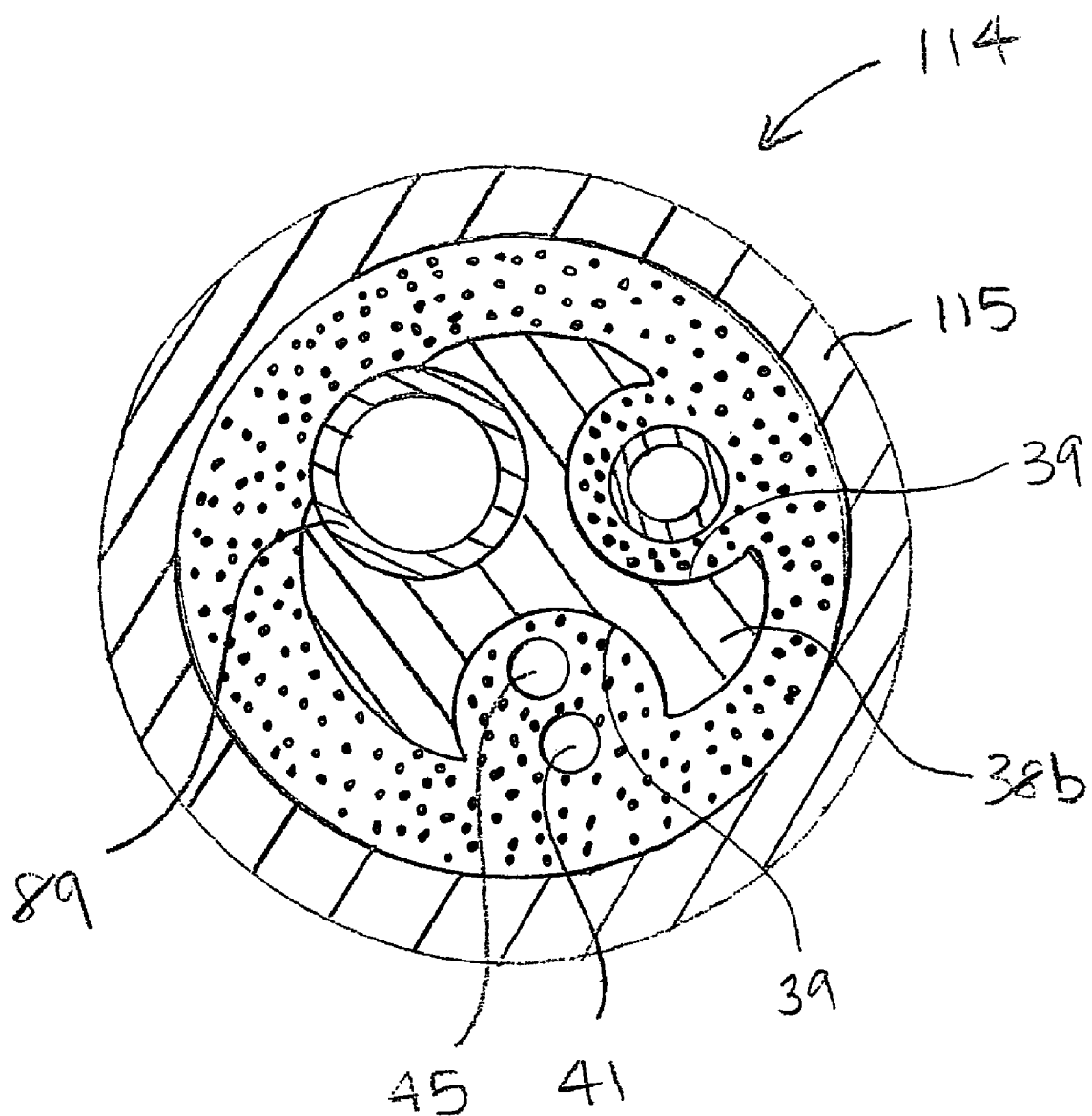
FIG. 10b is a longitudinal cross-sectional view of the tip section of FIG. 4c taken along line 10b-10b.
Figure 10C:
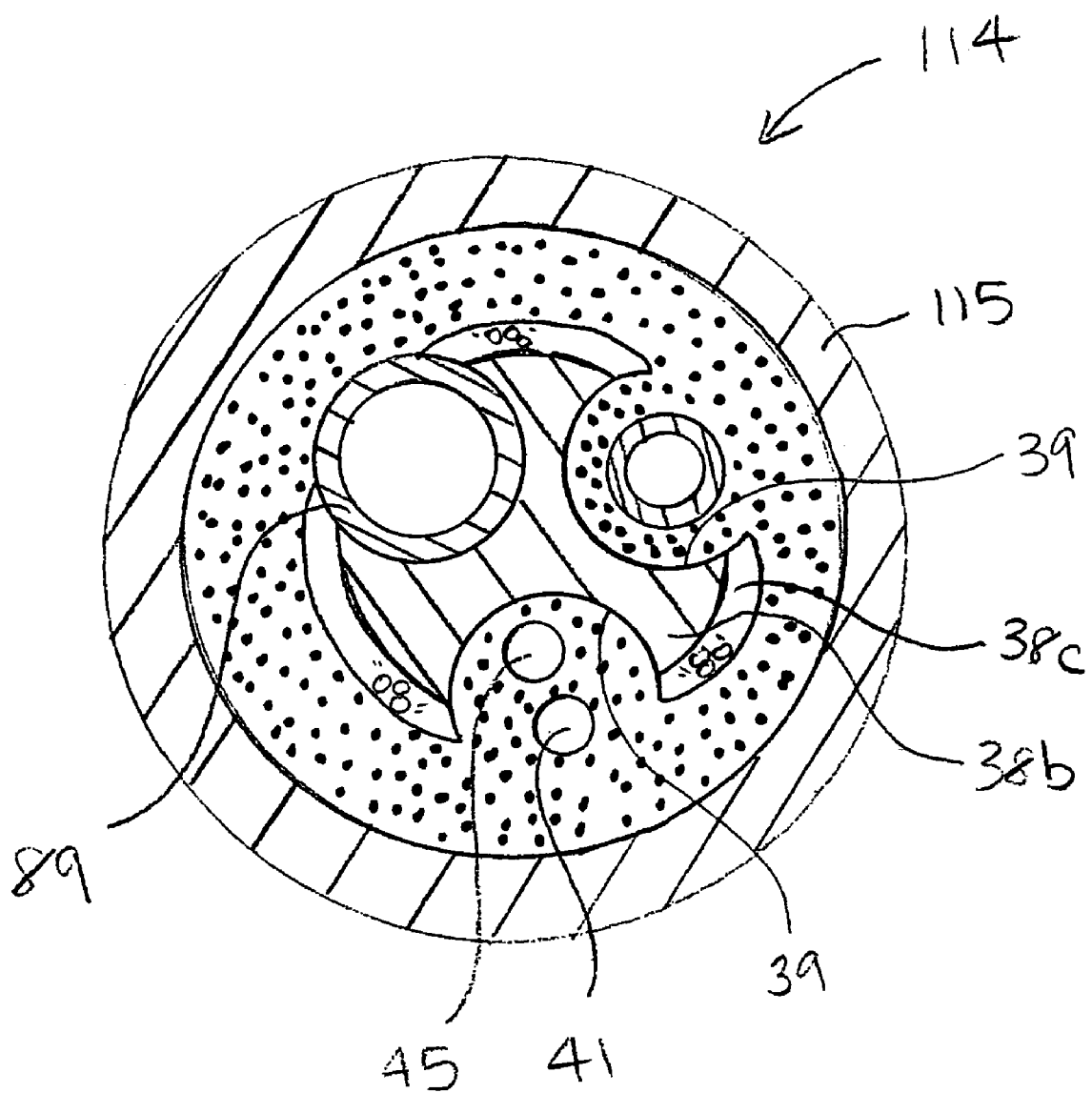
FIG. 10c is a longitudinal cross-sectional view of the tip section of FIG. 4c taken along line 10c-10c.

The conductive material of the stem 38b may further comprise a coating 38c made of the same porous material of the main electrode body 38a, as shown in FIG. 10c. In this embodiment, the stem 38b can be over-molded with the porous material to form the coating 38c. The coating 38c on the conductive material of the stem 38b provides increased structural stability of the tip electrode 38.

One or more ring electrodes 40 may be mounted along the length of the tip section. The length of the ring electrode 40 is not critical, but can range from about 1 mm to about 3 mm. If multiple ring electrodes are used, they can be spaced apart in any desired fashion so long as their edges do not touch.

Each ring electrode 40 is connected to a separate lead wire 30. In the two lumen tip section embodiment, each lead wire 30 extends through the second off-axis lumen 28 in the tip section 14, through the central lumen 18 in the catheter body 12 and through the control handle 16. In the three lumen tip section embodiment, the lead wires 30 extend through the third lumen 128 of the tip section 114. In the four lumen embodiment of the tip section, the lead wires 30 extend through the fourth lumen 129. The proximal end of each lead wire 30 extends out the proximal end of the control handle 16 and is connected to an appropriate connector (not shown), which can be plugged into or otherwise connected to a suitable monitor, source of energy, etc.

The lead wires 30 are connected to the ring electrodes 40 by any conventional technique. For example, connection of a lead wire 30 to a ring electrode is accomplished by first making a small hole through the tubing 24 and heating the needle sufficiently to form a permanent hole. A lead wire 30 is then drawn through the hole with a microhook or the like. The end of the lead wire 30 is then stripped of any coating and welded to the underside of the ring electrode 40, which is then slid into position over the hole and fixed in place with polyurethane glue or the like.

As shown in FIGS. 2, 3a and 4a, the lead wires 30 and 30a are enclosed within a protective sheath 62 to prevent contact with other components within the lumen of the catheter body 12. The protective sheath 62 can be made of any suitable material, for example polyimide. The protective sheath 62 is anchored at its distal end to the proximal end of the catheter body 12 by gluing it to the side wall of the catheter body 12 with polyurethane glue or the like. As would be recognized by one or ordinary skill in the art, the protective sheath 62 can be eliminated if desired.

The catheter may further comprise one or more temperature sensing means for sensing the temperature of the tip electrode and/or ring electrodes. Any conventional temperature sensing means, e.g. a thermocouple or thermistor, may be used. In one embodiment, as shown in FIGS. 3a and 4a, the temperature sensing means comprises a thermocouple formed by an enameled wire pair. One wire of the wire pair is a copper wire 41, e.g. a number 40 copper wire. The other wire of the wire pair is a constantan wire 45, which supports and strengthens the wire pair. The wires 41 and 45 of the wire pair are electrically isolated from each other except at their distal ends where they are twisted together, covered with a short piece of plastic tubing 43, e.g. polyimide tubing, and covered with epoxy. When used to sense the temperature of the tip electrode 38, the plastic tubing is attached in a blind hole in the tip electrode by polyurethane glue or the like. Alternatively, the plastic tubing 43 and wires 42 and 45 are placed in the tip electrode mold prior to injection of the porous polymer or plastic. The plastic is then injected into the mold over the plastic tubing 43 and wires 41 and 45, thereby anchoring the wire pair in the tip electrode. When used to sense the temperature of a ring electrode, the plastic tubing 43 is attached to the underside of the ring electrode by polyurethane glue or the like. In the two lumen tip section embodiment, the wires 41 and 45 extend through the second lumen 28 of the tip section 14, through the central lumen 18 of the catheter body 12 and into the control handle 16. The wires 41 and 45 extend through the control handle 16 to a connector (not shown) connectable to a temperature monitor.

Alternatively, the temperature sensing means may be a thermistor. A suitable thermistor for use in the present invention is Model No. AB6N2-GC14KA143E/37C sold by Thermometrics (New Jersey).

In another embodiment of the catheter 10, a puller wire 32 is provided for deflecting the tip section. In this embodiment, the tubing 124 of the tip section 114 comprises three lumens 126, 127 and 128. As shown in FIGS. 4a and 4b, the first lumen 126 carries an irrigation tube, the second lumen 127 carries a puller wire and the third lumen 128 carries any remaining wires, cables or tubes, including electrode lead wires and temperature sensor wires.

The puller wire 32 extends from the control handle 16, through the central lumen 18 of the catheter body 12 and into the second lumen 127 of the tip section 114. The proximal end of the puller wire 32 is anchored within the control handle 16 and the distal end of the puller wire 32 is anchored in the tip electrode 38 or in the tip section 114.

The puller wire 32 is made of any suitable metal, such as stainless steel or Nitinol. In one embodiment, the puller wire 32 has a coating 33, such as Teflon® or the like. The puller wire 32 has a diameter ranging from about 0.006 inch to about 0.0010 inch.

Figure 5:
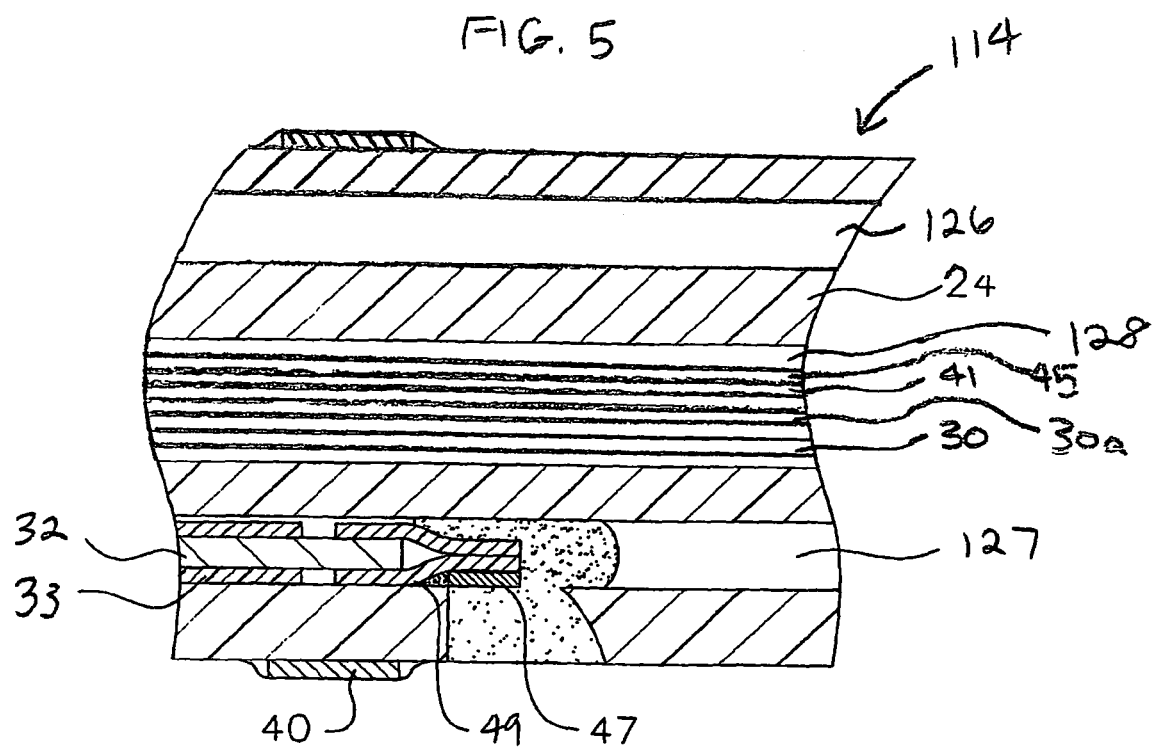
FIG. 5 is a side cross-sectional view of a catheter tip section according to one embodiment of the present invention where the puller wire is anchored to the side wall of the tip section.
Figure 6:
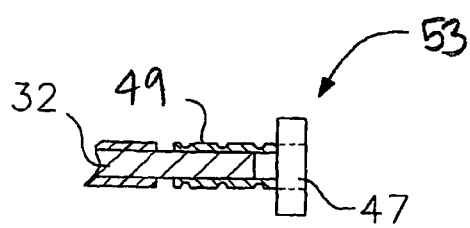
FIG. 6 is a longitudinal cross-sectional view of an exemplary puller wire T-bar anchor.
Figure 7:
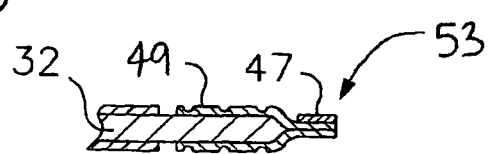
FIG. 7 is a longitudinal cross-sectional view of the T-bar anchor of FIG. 6 rotated 90° to show the cross piece on end.

In the embodiment depicted in FIGS. 4a and 4b, the puller wire 32 is anchored in a blind hole in the tip electrode 38. Alternatively, the puller wire 32 can be anchored to the side wall of the tip section 114, as shown in FIGS. 5, 6 and 7. In this alternative arrangement, the puller wire 32 is attached to the side wall by means of an anchor 53 fixedly attached to the distal end of the puller wire 32. The anchor 53 is formed by a metal tube 49, e.g., a short segment of hypodermic stock, that is fixedly attached, e.g. by crimping, to the distal end of the puller wire 32. The tube has a section that extends a short distance beyond the distal end of the puller wire 32. A crosspiece 47 made of a small section of stainless steel ribbon or the like is soldered or welded in a transverse arrangement to the distal end of the metal tube which is flattened during the operation. This creates a T-bar anchor 53. A notch is created in the side of the tip section 114 resulting in an opening in the lumen carrying the puller wire 32. The cross-piece 47 lies transversely within the notch. Because the length of the ribbon forming the cross-piece 47 is longer than the diameter of the opening into the lumen, the anchor 53 cannot be pulled completely into the lumen. The notch is then sealed with polyurethane glue or the like to give a smooth outer surface. The glue flows into the lumen to fully secure the anchor. A tunnel (not shown), in the form of polyimide tubing or the like, can be provided to permit passage of the lead wires 30 through the glue. Other means for anchoring the puller wire 32 in the tip section would be recognized by those skilled in the art and are included within the scope of this invention.

The catheter 10 may further comprise a compression coil 46 in surrounding relation to the puller wire 32. The compression coil 46 is made of any suitable metal, such as stainless steel. The compression coil 46 is tightly wound on itself to provide flexibility, i.e. bending, but to resist compression. The inner diameter of the compression coil 46 is slightly larger than the diameter of the puller wire. For example, when the puller wire has a diameter of about 0.007 inch, the compression coil has an inner diameter of about 0.008 inch. The coating on the puller wire 32 allows them to slide freely within the compression coil 46. The outer surface of the compression coil 46 is covered along most of its length by a flexible non-conductive sheath 48 to prevent contact between the compression coil 46 and the lead wires 30 and 31 within the central lumen 18 of the catheter body 12. One example of a suitable material for the non-conductive sheath 48 is thin-walled polyimide tubing.

At the distal end of the catheter body 12, the compression coil 46 is aligned with the second lumen 127 into which the puller wire 32 extends. The compression coil 46 and stiffening tube 22 are sized so that the compression coil fits closely and slidably within the stiffening tube 22. With this design, the lead wires 30 and 31 can distribute themselves around the compression coil 46 without misaligning the coil.

The compression coil 46 is secured within the catheter body 12 with polyurethane glue or the like. The compression coil 46 is anchored at its proximal end to the proximal end of the stiffening tube 22 in the catheter body 12 by a proximal glue joint (not shown). When a stiffening tube is not used, the compression coil 46 is anchored directly to the outer wall 20 of the catheter body 12.

The distal end of the compression coil 46 is anchored to the proximal end of its corresponding lumen in the tip section by distal glue joint 52. Alternatively, the distal end of the compression coil 46 may be anchored to the distal end of the stiffening tube 22 in the catheter body or directly to the distal end of the outer wall 20 of the catheter body 12 when no stiffening tube is used. In the depicted embodiment, where the compression coil 46 is surrounded by a sheath 48, care should be taken to ensure that the sheath is reliably glued to the compression coil. The lead wires 30 and 31 can also be anchored in the glue joint. However, if desired, tunnels in the form of plastic tubing or the like can be provided around the lead wires at the glue joint to permit the lead wires to be slidable within the glue joint.

Both glue joints comprise polyurethane glue or the like. The glue may be applied by means of a syringe or the like through a hole made between the outer wall 20 of the catheter body 12 and the central lumen 18. Such a hole may be formed, for example, by a needle or the like that punctures the outer wall 20 and stiffening tube 22 and is heated sufficiently to form a permanent hole. The glue is then introduced through the hole to the outer surface of the compression coil 46 and wicks around the outer circumference to form a glue joint about the entire circumference of the sheath 48 surrounding the compression coil 46. Care should be taken to ensure that glue does not wick over the end of the coil, preventing the puller wire from sliding within the coil.

Within the lumen of the tip section, the puller wire 32 is surrounded by a plastic sheath 42, which can be made of Teflon®. The plastic sheath 42 prevents the puller wire 32 from cutting into the side wall of the tip section when the tip section is deflected. The sheath 42 ends near the distal end of the puller wire 32. Alternatively, the puller wire 32 can be surrounded by a compression coil where the turns are expanded longitudinally, relative to the compression coil 46 extending through the catheter body, such that the surrounding compression coil is both bendable and compressible.

Longitudinal movement of the puller wire 32 relative to the catheter body 12, which results in deflection of the tip section 114, is accomplished by suitable manipulation of the control handle 16. A suitable control handle for use with the present invention is described in U.S. Pat. No. 6,120,476, the entire content of which is incorporated herein by reference.

The catheter 10 may further comprise an electromagnetic sensor 72 mounted in the tip section. As shown in FIGS. 3c and 4c, in this embodiment, the tip electrode 38 is connected to the tubing 24 and 124 of the tip section by means of a plastic housing 115, which can be made of polyetheretherketone (PEEK). The stem 38b of the tip electrode 38 fits inside the distal end of the plastic housing 115, leaving space between the wall of the stem 38b and the plastic housing 115. The stem 38b of the tip electrode 38 is potted in the plastic housing 115 with polyurethane glue or the like. The proximal end of the plastic housing 115 is bonded to the distal end of the tubing of the tip section with polyurethane glue or the like.

One or more ring electrodes 40 can be mounted on the plastic housing 115. Lead wires 30 are attached to the ring electrodes 40 generally as described above.

The electromagnetic sensor 72 is connected to an electromagnetic sensor cable 74, which extends through a lumen of the tip section. When the tip section has two lumens, the cable 74 extends through the second lumen 28. When the tip section has three lumens, the cable 74 extends through the third lumen 128. From the tip section, the electromagnetic sensor cable 74 extends through the central lumen 18 of the catheter body and out through the control handle 16. The electromagnetic sensor cable 74 then extends out the proximal end of the control handle 16 within an umbilical cord (not shown) to a sensor control module (not shown) that houses a circuit board (not shown). The electromagnetic sensor cable 74 comprises multiple wires encases within a plastic covered sheath. In the sensor control module, the wires of the electromagnetic sensor cable 74 are connected to the circuit board. The circuit board amplifies the signal received from the electromagnetic sensor 72 and transmits it to a computer in a form understandable by the computer. Because the catheter is designed for a single use only, the circuit board may contain an EPROM chip which shuts down the circuit board approximately 24 hours after the catheter has been used. This prevents the catheter, or at least the electromagnetic sensor from being used twice.

Suitable electromagnetic sensors for use with the present invention are described, for example, in U.S. Pat. Nos. 5,558,091, 5,443,489, 5,480,422, 5,546,951, 5,568,809 and 5,391,199 and International Publication No. WO 95/02995, the entire contents of which are incorporated herein by reference. One exemplary electromagnetic sensor 72 has a length of from about 6 mm to 7 mm and a diameter of about 1.3 mm.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support for the following claims which are to have their fullest and fairest scope

What is claimed is:

1. An irrigated catheter comprising:
 a catheter body having proximal and distal ends and at least one lumen extending therethrough;
 a tip section comprising a segment of flexible tubing having proximal and distal ends and at least two lumens extending therethrough, the proximal end of the tip section being fixedly attached to the distal end of the catheter body;
 a porous tip electrode fixedly attached to the distal end of the tip section, the tip electrode comprising a main electrode body and a stem, wherein at least the main electrode body comprises a porous material covered in parts by an outer skin to form a pattern on the main electrode body;
 a first irrigation tube segment having proximal and distal ends extending through the catheter body, the distal end of the irrigation tube being anchored near the proximal end of the tip section;
 a second irrigation tube segment having proximal and distal ends, the proximal end of the second irrigation tube segment being anchored near the distal end of the tip section and the distal end of the second irrigation tube segment being anchored in the tip electrode, whereby fluid passing through the first and second irrigation tube segments can pass through the porous material of the tip electrode to reach surrounding tissue; and
 means for energizing the fluid passing through the first and second irrigation tube segments.

2. An irrigated catheter according to claim 1, wherein the means for energizing the fluid comprises an inner conductive sleeve on an inner surface of the second irrigation tube segment and an electrode lead wire connected to the inner conductive sleeve.

3. An irrigated catheter according to claim 2, wherein the electrode lead wire extends from the sleeve of the stem of the tip electrode through a channel between the stem and the tubing of the tip section and into the second lumen of the tip section.

4. An irrigated catheter according to claim 1, wherein the stem of the tip electrode comprises a conductive material and the means for energizing the fluid comprises a lead wire connected to the stem.

5. An irrigated catheter according to claim 1, further comprising a temperature sensing means mounted within the tip electrode.

6. An irrigated catheter according to claim 1, further comprising an electromagnetic sensor.

7. An irrigated catheter according to claim 1, further comprising at least one ring electrode mounted on the tip section.

8. An irrigated catheter according to claim 7, further comprising a temperature sensing means mounted to the at least one ring electrode.

9. An irrigated catheter according to claim 1, wherein the tip electrode comprises an injection molded porous plastic material.

10. An irrigated catheter comprising:
 a catheter body having proximal and distal ends and at least one lumen extending therethrough;
 a tip section comprising a segment of flexible tubing having proximal and distal ends and at least two lumens extending therethrough, the proximal end of the tip section being fixedly attached to the distal end of the catheter body;
 a porous tip electrode fixedly attached to the distal end of the tip section, the tip electrode comprising a main electrode body and a stem, wherein at least the main electrode body comprises a porous material covered in parts by an outer skin to form a pattern on the main electrode body, wherein the porous material is selected from the group consisting of polyethylene, polypropylene, ethylene vinyl acetate, polystyrene, epoxy glass, phenol glass and mixtures thereof;
 a first irrigation tube segment having proximal and distal ends extending through the catheter body, the distal end of the irrigation tube being anchored near the proximal end of the tip section;
 a second irrigation tube segment having proximal and distal ends, the proximal end of the second irrigation tube segment being anchored near the distal end of the tip section and the distal end of the second irrigation tube segment being anchored in the tip electrode, whereby fluid passing through the first and second irrigation tube segments can pass through the porous material of the tip electrode to reach surrounding tissue; and
 means for energizing the fluid passing through the first and second irrigation tube segments.

11. A tip electrode for a catheter, the tip electrode comprising:
 a main electrode body having proximal and distal ends and comprising a porous material covered in parts by an outer skin to form a pattern in the main electrode body; and
 a stem extending from the proximal end of the main electrode body.

12. A tip electrode according to claim 11, wherein the stem comprises the same material as the main electrode body.

13. A tip electrode according to claim 11, wherein the stem comprises a conductive material.

14. A tip electrode according to claim 13, wherein the stem is coated with a porous material.

15. A tip electrode according to claim 11, wherein the porous material is selected from the group consisting of polyethylene, polypropylene, ethylene vinyl acetate, polystyrene, epoxy glass, phenol glass and mixtures thereof.

16. A tip electrode according to claim 11, wherein the tip electrode comprises an injection molded porous plastic material.

17. A method of manufacturing the tip electrode of claim 11, the method comprising:
- placing a porous material in a hopper;
- feeding the porous material from the hopper into an injection barrel;
- heating the injection barrel to soften the porous material;
- forcing the softened porous material through a nozzle at an end of the injection barrel into a mold;
- cooling the porous material in the mold to form the tip electrode;
- ejecting the tip electrode from the mold, wherein the ejected tip electrode comprises an outer skin on an outer surface of the tip electrode; and
- removing a portion of the outer skin of the tip electrode to thereby form a pattern in the tip electrode.

* * * * *